(12) United States Patent
Zhao et al.

(10) Patent No.: US 8,573,064 B2
(45) Date of Patent: Nov. 5, 2013

(54) MAGNETIC SUSPENSION SUPPORTER OF DIRECT TENSION TEST APPARATUS

(75) Inventors: Zhonghu Zhao, Lanzhou (CN); Xiaojing Zheng, Lanzhou (CN); Youhe Zhou, Lanzhou (CN)

(73) Assignee: Lanzhou University, Lanzhou, Gansu Province (CN)

( * ) Notice: Subject to any disclaimer, the term of this patent is extended or adjusted under 35 U.S.C. 154(b) by 92 days.

(21) Appl. No.: 13/127,397

(22) PCT Filed: Jan. 16, 2010

(86) PCT No.: PCT/CN2010/070232
§ 371 (c)(1),
(2), (4) Date: May 3, 2011

(87) PCT Pub. No.: WO2010/083745
PCT Pub. Date: Jul. 29, 2010

(65) Prior Publication Data
US 2011/0259113 A1    Oct. 27, 2011

(30) Foreign Application Priority Data
Jan. 20, 2009   (CN) .......................... 2009 1 0105154

(51) Int. Cl.
*G01N 3/02* (2006.01)
*G01L 1/00* (2006.01)

(52) U.S. Cl.
USPC .................... 73/856; 73/860; 73/831; 73/781

(58) Field of Classification Search
USPC ................... 73/779, 856, 860, 826, 831, 781, 73/862.42, 862.392, 862.69
See application file for complete search history.

(56) References Cited

U.S. PATENT DOCUMENTS

| | | | | |
|---|---|---|---|---|
| 6,041,667 A * | 3/2000 | Pischinger et al. | ........ | 73/862.69 |
| 6,617,722 B2 * | 9/2003 | Ooyama et al. | ............ | 310/68 B |
| 6,844,721 B2 * | 1/2005 | Oliver | ...................... | 324/207.17 |
| 7,148,432 B2 * | 12/2006 | Mori | ...................... | 177/210 EM |
| 7,543,506 B2 * | 6/2009 | Merendino, Sr. | ............... | 73/779 |
| 7,568,397 B2 * | 8/2009 | Merendino, Sr. | ............... | 73/856 |

* cited by examiner

*Primary Examiner* — Lisa Caputo
*Assistant Examiner* — Jonathan Dunlap
(74) *Attorney, Agent, or Firm* — Jackson IPG PLLC

(57) ABSTRACT

A magnetic suspension supporter for a direct tension test apparatus, includes an upper end cap and a lower end cap for fixing a sample, an upper chain and a lower chain connected to the upper and lower end caps respectively, an upper joint and a lower joint connected to the other ends of the upper and lower chains respectively, the lower joint being fixed to the test machine foundation. In addition, the upper and lower end caps, the upper and lower chains, the upper and lower joints as well as the supporter having a common vertical axis and being arranged in a cascade form, characterized in that a sample supporter is arranged between the lower end cap and the test machine foundation. The sample supporter is composed of a pair of upper magnet provided at the underside of the lower end cap and lower magnet on the upside of the test machine foundation, which constitute two magnets structure. The polarity directions of the two magnets are reversed and the same polarity is arranged oppositely on the axis. The following technical effect is realized: sudden breaking caused by the gravity when peak stress is reached may be prevented; the magnet is fixed to the axis, which may prevent the sample from being destroyed at the end portion due to the left and right swaying of the spring, ensuring accuracy of the test data.

9 Claims, 2 Drawing Sheets

MAGNETIC SUSPENSION SUPPORTER OF DIRECT TENSION TEST APPARATUS

FIELD OF THE INVENTION

The present invention relates to a direct tension test apparatus for a brittle material, and particularly to a supporter of this experimental apparatus.

BACKGROUND OF THE INVENTION

A direct tension test apparatus is typically used when the tensile mechanical property is measured for the brittle material such as the rock. FIG. 1 shows a supporter of a conventional tension test apparatus. When the tension test is performed by using this apparatus, the rigidity sleeve 4 can not support the weight of sample 8 and lower end cap 7 effectively. Therefore, when the force applied to the sample reaches a peak value, under the gravity effect on the sample, lower end cap and lower chain under the breaking plane, sudden breaking occurs to the sample, and the measurement of the material mechanical property after peak stress may not be performed. In order to solve such problem, the Chinese patent application No. 200610022224.8 discloses a technical solution which uses a support spring 8 to replace the rigidity sleeve 4 (shown in FIG. 2), in this way, throughout the tension test, the weight of sample 5 and other test components is supported by the spring 8 and the measurement of the whole process curve may substantially be completed. However, some new problems may be introduced by using this spring supporter and the problems mainly include: 1) the sample is broken at the end portion. Theoretically, breaking should occur in the middle of the sample. However, from the whole process of the tension test, during the tension process, the test data will be influenced due to the left and right sway of the spring and chain, which becomes more prominent especially during the test near the peak stress and after the peak value. In this case, the sample is broken at the end portion, which actually does not reflect the mechanical property of the brittle material during the whole tension process; 2) the applicability is poor. There is no corresponding stipulation on the sample size and specification of the direct tension test, so the volumes, weights, tensile strengths and so on of the samples may be considerably different, and thereby different support forces may be required for the supporters. For example, a spring with a larger stiffness coefficient may not be suitable for a small sample which is subject to tensile failure, otherwise it is the same as the rigidity supporter; on the contrary, a spring with a extremely small stiffness coefficient may not be suitable for a large sample which is not subject to tensile failure, otherwise the spring may be out of action. Therefore, many springs are required to be prepared for various samples, and there is a need for replacing the spring continuously when the tension tests are continuously performed for different samples, which increase the complexity of operation; 3) installation procedure is complex. As shown in FIG. 1, from the test process, when a test is completed and the next test is to be performed, the upper and lower bolts need to be taken down for replacing the sample, and then be mounted again. It can be seen from the figure, the lower joint, the lower bolt and the chain are enclosed by the spring. The space within the spring is strait and the interval between two rings is also small, which introduces inconveniences to the installation of the lower components; 4) distortion and aging may occur to the spring during the long time use, which may affect the performance of the spring. According to the above reasons, it is necessary to seek a supporter of the tension test apparatus which may overcome these drawbacks of the spring.

SUMMARY OF THE INVENTION

The object of the present invention is to provide a magnetic suspension supporter of a direct tension test apparatus for overcoming the drawbacks existing in the spring supporter of the tension test apparatus in the prior art.

The magnetic suspension supporter includes: an upper end cap and a lower end cap for fixing a sample, an upper chain and a lower chain connected to the upper and lower end caps respectively, an upper joint and a lower joint connected to the other ends of the upper and lower chains respectively, the lower joint being fixed to the test machine foundation; the upper and lower end caps, the upper and lower chains as well as the upper and lower joints having a common vertical axis and being arranged in a cascade form, characterized in that a sample supporter is arranged between the lower end cap and the test machine foundation. The sample supporter is composed of a pair of upper magnet provided at the underside of the lower end cap and lower magnet on the upside of the test machine foundation, which constitute two magnets structure. The polarity directions of the two magnets are reversed and the same polarity thereof are arranged oppositely on the axis. Because of the same polarity on the opposite surfaces of the two magnets, they are separated under the exclusive force and may implement relative movement.

In the above technical solution, upper and lower separating-proof bolts are arranged between the upper/lower chains and the upper/lower end caps, respectively.

In the above technical solution, the two magnets are composed of a pair of column-shaped magnets which have circular sections and may be hitched on the lower chain, wherein the upper magnet may slide up and down along the lower chain as an axis.

In the above technical solution, the two magnets are permanent magnets, or at least one of the upper and lower magnets is an electromagnet.

In the above technical solution, for the two magnets, there is a magnetic insulation plate on the upside of the upper magnet and the underside of the lower magnet, respectively.

In the above technical solution, there is a magnetic insulation sleeve with a smooth outer surface outside the lower chain, the upper magnet has smooth internal wall and is hitched on the magnetic insulation sleeve, being capable of sliding up and down.

In the above technical solution, there is a magnetic insulation cover outside the two magnets.

In the above technical solution, in the case where one magnet of the two magnets is a electromagnet, at the start of the test, a current strength which generates directional magnetic force is applied slowly, and gradually increased magnetic strength is generated, which causes the two magnets to be separated because of the exclusive force; at the end of the test, the current strength applied to the electromagnet is weakened slowly and the magnetic strength is reduced gradually, which causes the two magnets to approach each other because of the reduced exclusive force, finally, the current on the electromagnet disappears and the two magnets contact each other due to the elimination of the exclusive force.

In the above technical solution, there is a holding frame between the two magnets which is used to support the test components on the upside of the supporter of the tension test apparatus in the case where the electromagnet has no magnetic force because no current is applied.

In the above technical solution, there is a gravity detection alarm apparatus on the holding frame. If the weight of the object on the holding frame exceeds a limitation, the alarm is triggered, and an alarm signal is emitted through buzzer or indicator lamp.

The following technical effects may be achieved in the present invention:

1. In the tension test, the two magnets are arranged in the same polarity direction, the opposite planes of the two magnets are mutually exclusive because of the same polarity, the generated exclusive force holds the sample and other components on the upper side. The two magnets with sufficient magnetic strength are adopted to ensure substantial balance between the generated exclusive force and the sum of gravities of the sample and components at the underside of the breaking plane, which realizes the effect of the spring supporter and prevents the sample from being destroyed suddenly; in addition, the upper magnet in the two magnets is fixed to an axis to slide up and down without swaying left and right, which may prevent the sample from being destroyed at the end portion and ensure accuracy of the test data; furthermore, the two magnets have low cost and long life, the lose of the device is small and installation in the test process is simple. Particularly, when the electromagnet is adopted, the magnetic strength may be adjusted conveniently only by adjusting the current applied to the electromagnetic coil, which is suitable for a flexible test with different samples;

2. Upper and lower separating-proof bolts are arranged between the upper/lower chains and the upper/lower end caps, respectively, which further ensures the security of the connection;

3. The technical feature in which the two magnets are composed of a pair of column-shaped magnets which have circular sections and may be hitched on the lower chain, wherein the upper magnet may slide up and down along the lower chain as an axis, ensures the adjustment of the interval between the two magnets and increases its applicability;

4. At least one of the two magnets is set to be an electromagnet, and the magnetic strength may be controlled by controlling the magnitude and existence of the current, which further increases its applicability;

5. For the two magnets, there is a magnetic insulation plate on the upside of the upper magnet and the underside of the lower magnet, respectively; there is a magnetic insulation sleeve with a smooth outer surface outside the lower chain, the upper magnet has smooth internal wall and is hitched on the magnetic insulation sleeve, being capable of sliding up and down. The above technical feature may avoid interference from the outside and further increases the accuracy of the measurement;

6. There is a gravity detection alarm apparatus on the holding frame. If the weight of the object on the holding frame exceeds a limitation, the alarm is triggered, and an alarm signal is emitted through buzzer or indicator lamp, which further enhances the security and operability of the apparatus.

DETAILED DESCRIPTION OF THE EMBODIMENTS

For conveniently understanding and implementing the present invention by those skilled in the art, the present invention will be further described in detail with reference to the figures and embodiments.

Figure 1:
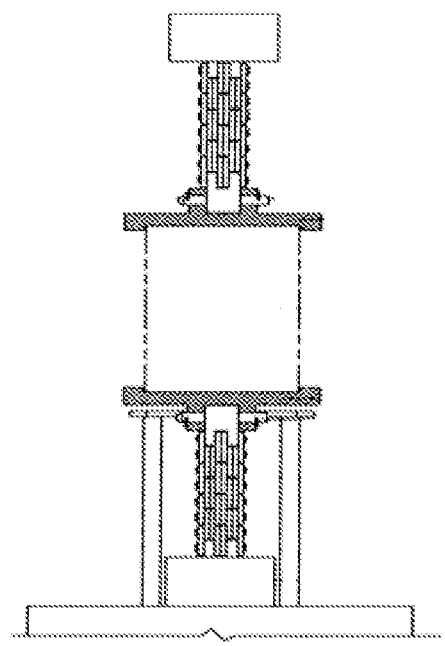
FIG. 1 is a schematic diagram illustrating the structure of a direct tension test apparatus according to the prior art.
Figure 2:
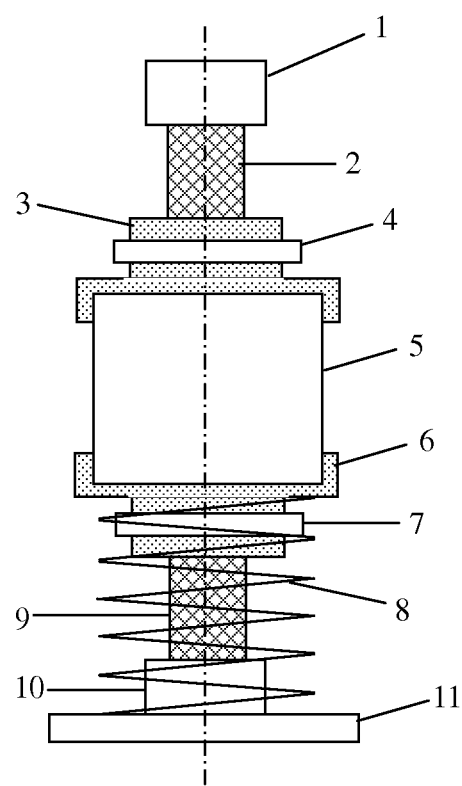
FIG. 2 is a schematic diagram illustrating the structure of a spring support type tension apparatus in the direct tension test according to the prior art.
Figure 3:
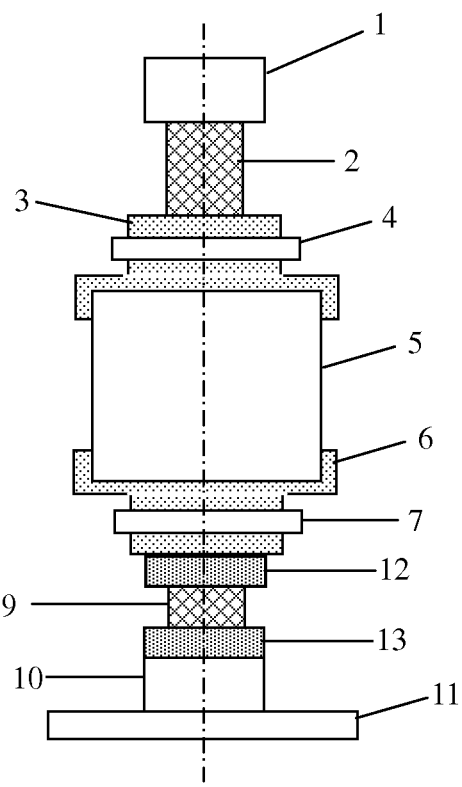
FIG. 3 is a schematic diagram illustrating the structure of a magnetic suspension supported tension apparatus in the direct tension test according to the present invention.

FIG. 3 shows the test apparatus of the present invention. This apparatus includes the following components: an upper end cap 3 and a lower end cap 6 for fixing a sample 5, an upper chain 2 and a lower chain 9 connected to the upper and lower end caps respectively, an upper bolt 4 and a lower bolt 7 for preventing the sample-close ends of the upper and lower chains (i.e., the ends of the chains close to the sample) from separating from the corresponding end caps, an upper joint 1 and a lower joint 10 connected to the other ends of the upper chain 2 and lower chain 9, respectively, the lower joint 10 being fixed to the test machine foundation 11. The components between the lower end cap 6 and the test machine foundation 11 constitute the sample supporter used in the test. The upper end cap 3 and lower end cap 6, the upper chain 2 and lower chain 9, the upper joint 1 and lower joint 10 as well as the supporter have a common vertical axis and are arranged in a cascade form. The sample supporter includes two magnets which are composed of a pair of upper magnet 12 and lower magnet 13 (see FIG. 4). The two magnets are located on the axis and the polarity directions thereof are reversed. Because of the same polarity on the opposite surfaces of the two magnets, they are separated under the exclusive force, and may implement relative movement.

In the tension test, the two magnets are arranged in the same polarity direction, the opposite planes of the two magnets are mutually exclusive because of the same polarity, and the generated exclusive force holds the sample and other components on the upper side. The two magnets with sufficient magnetic strength are adopted to ensure that the generated exclusive force is larger than the sum of the peak value of the tension when the sample is broken because of the tension and gravities of the sample and components at the underside of the breaking plane. In addition, the upper magnet of the two magnets is fixed to an axis to slide up and down, thus, in the whole test, if the sample is broken, the exclusive force generated by the two magnets may sufficiently counteract the interference of the sample which affects the data deviation when the sample is broken because of the tension.

Embodiment 1

Permanent Magnet Supporter

Figure 4:
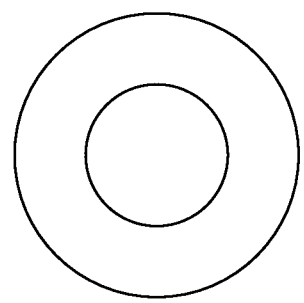
FIG. 4 is a stereogram of the magnetic components according to the present invention.
Figure 5:
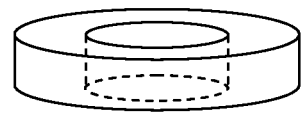
FIG. 5 is a top view of the FIG. 4.

Referring to FIGS. 4 and 5, the two magnets are composed of a pair of column-shaped magnets which have circular sections, there is a magnetic insulation sleeve with a smooth outer surface outside the lower chain 9, the upper magnet 12 has smooth internal wall and is hitched on the lower chain 9 at the outside of the magnetic insulation sleeve, being capable of sliding up and down along the lower chain 9 as an axis.

The two magnets may be permanent magnets. Magnets with different magnetic strengths may be configured according to the samples 5 with different tensile strengths, which is convenient for selection in the test.

For the two magnets, there is a magnetic insulation plate on the upside of the upper magnet 12 and the underside of the lower magnet 13, respectively, to eliminate influence of the magnets on the other magnetizable components. There may be a cylinder-shaped magnetic insulation cover outside the two magnets for enclosing both of the two magnets, which eliminates influence of the magnetic field generated by the magnet on the surrounding environment and other instruments. One end of the magnetic insulation cover is fixed to the outer surface of one of the magnets and the other end is free; or two cylinder-shaped magnetic insulation covers, which have suited internal diameters and may be coupled in piston form, may be adopted, both ends thereof are fixed to the outer surface of the magnets. In this way, it is possible for the two magnets to move within the magnetic insulation cover and the magnetic field may not leak out.

Embodiment 2

Electromagnet Supporter

The permanent magnet in the embodiment 1 may be replaced by the electromagnet. One of the upper magnet 12 and the lower magnet 13 may be replaced by the electromagnet, or both of the magnets may be replaced by the electromagnet. The electromagnet supporter has more excellent test operation performance and test flexibility. It is possible for the polarity and magnetic strength of the electromagnet to be adjusted arbitrarily by adjusting the current applied to the electromagnet, and the different exclusive forces generated may be suitable for different sample to be tested. In addition, it is convenient for the electromagnet to be controlled through a microcomputer program, which may improve the intelligence and automatization degree. For example:

At the start of the test, a current strength which generates directional magnetic force is applied slowly, and gradually increased magnetic strength is generated, which causes the two magnets to be separated because of the exclusive force; at the end of the test, the current strength applied to the electromagnet is weakened slowly and the magnetic strength is reduced gradually, which causes the two magnets to approach each other gradually because of the reduced exclusive force, finally, the current on the electromagnet disappears and the two magnets contact each other due to the elimination of the exclusive force. Changing process of the magnetic exclusive force may be collected automatically by a computer during the tension test, and thereby more valuable test data may be obtained.

When the electromagnet is applied, in the case where the electromagnet has no magnetic force because no current is applied, the upper magnet 12 contacts the lower magnet 13 due to the gravity force. A holding frame is required to be located between the two magnets for supporting the test components and sample 5 on the upside of the supporter of the tension test apparatus. This holding frame may be a spring, which may protect the test components and sample 5 on the upside of the supporter of the test apparatus when the electromagnet suddenly fails due to an unexpected power supply failure during the test process. The spring has buffer action for preventing the test apparatus from being destroyed when contingency occurs, otherwise, in the tension process, if the power supply to the electromagnet suddenly stops due to unexpected failure, the upper magnet as well as the components and sample above the upper magnet may strike the lower magnet fiercely.

The following improvement may be implemented for the above two embodiments:

Tension Breaking Alarm

In the direct tension test for brittle materials, if the magnet is unsuitable, for example, the exclusive force is too small to support the breaking sample and the components under the sample, the two magnets will strike each other directly, which results in failure of the test and possible damage of the instrument. Therefore, in the present invention, a gravity detection alarm apparatus is added on the holding frame of the embodiment 2. If it is detected that the weight of the object on the holding frame 18 exceeds a limitation, the alarm is triggered, and an alarm signal is emitted through buzzer or indicator lamp. Reasonable alarm parameters may be configured according to actual conditions of the tension test, such as the gravity ultimate parameter. According to the type, size, physical parameters of the sample and other study results, the tension peak value data when the sample is broken may be estimated, which may be converted into an initial gravity ultimate parameter of the tension test. For example, for a particular sample, if the total weight of the sample under the breaking plane and the lower clamp part is 100 N, the maximum exclusive force of the two magnets is required to be not less than 100 N, and for security, the maximum exclusive force of the two magnets needs to be 120 N. Of course, it is unsuitable for the parameter to be unduly large, otherwise the sensitivity for collecting data will be reduced and certain waste may be produced, for example, a large current is supplied to the magnet for power supply. Various sample parameters may be input to the computer of the tension apparatus in advance to setup an analysis data base.

In the tension test, if the experimenter selects the strength parameter of the initial magnet (permanent magnet or electromagnet) unsuitably (too large or too small), the gravity detection alarm apparatus in the present invention will detect such event and start alarm to prompt the experimenter to correct the magnetic strength. For the electromagnet, a suitable magnetic strength parameter may be configured automatically by the computer processing system of the tension apparatus in order to complete the test successfully.

The invention claimed is:
1. A magnetic suspension supporter for a direct tension test apparatus, comprising:
an upper end cap and a lower end cap for fixing a sample, an upper chain and a lower chain connected to the upper and lower end caps respectively, an upper joint and a lower joint connected to the other ends of the upper and lower chains respectively, the lower joint being fixed to the test machine foundation;
the upper end cap and lower end cap, the upper chain and lower chain as well as the upper joint and lower joint having a common vertical axis and being arranged in a cascade form, characterized in that a sample supporter is arranged between the lower end cap and the test machine foundation, the sample supporter has two magnets structure which comprises a pair of upper magnet provided at the underside of the lower end cap and lower magnet on the upside of the test machine foundation, the polarity directions of the two magnets are reversed and the same polarity are arranged oppositely on the axis, and the two magnets implement relative movement;
wherein a separating-proof upper bolt and a separating-proof lower bolt are arranged between the upper/lower chains and the upper/lower end caps, respectively.
2. The magnetic suspension supporter for a direct tension test apparatus according to claim 1, wherein the two magnets are composed of a pair of column-shaped magnets which have circular sections and are hitched on the lower chain, wherein the upper magnet slides up and down along the lower chain as an axis.

3. The magnetic suspension supporter for a direct tension test apparatus according to claim 1, wherein the two magnets are permanent magnets, or at least one of the upper magnet and lower magnet is an electromagnet.

4. The magnetic suspension supporter for a direct tension test apparatus according to claim 3, wherein, in the case where one of the two magnets is a electromagnet, at the start of the test, a current strength which generates directional magnetic force is applied slowly, and gradually increased magnetic strength is generated, which causes the two magnets to be separated because of the exclusive force;

at the end of the test, the current strength applied to the electromagnet is weakened slowly and the magnetic strength is reduced gradually, which causes the two magnets to approach each other because of the reduced exclusive force, finally, the current on the electromagnet disappears and the two magnets contact each other due to the elimination of the exclusive force.

5. The magnetic suspension supporter for a direct tension test apparatus according to claim 3, wherein, there is a holding frame between the two magnets, which is used to support test components on the upside of the supporter of the tension test apparatus in the case where the electromagnet has no magnetic force because no current is applied.

6. The magnetic suspension supporter for a direct tension test apparatus according to claim 1, wherein, for the two magnets, there is a magnetic insulation plate on the upside of the upper magnet and the underside of the lower magnet, respectively.

7. The magnetic suspension supporter for a direct tension test apparatus according to claim 1, wherein, there is a magnetic insulation sleeve with a smooth outer surface outside the lower chain, the upper magnet has smooth internal wall and is hitched on the magnetic insulation sleeve, sliding up and down.

8. The magnetic suspension supporter for a direct tension test apparatus according to claim 1, wherein, there is a magnetic insulation cover outside the two magnets.

9. The magnetic suspension supporter for a direct tension test apparatus according to claim 1, wherein, there is a gravity detection alarm apparatus on the holding frame, if it is detected that the weight of the object on the holding frame exceeds a limitation, the alarm is triggered, and an alarm signal is emitted through buzzer or indicator lamp.

* * * * *